United States Patent [19]
Cohen

[11] Patent Number: 5,662,512
[45] Date of Patent: Sep. 2, 1997

[54] POSTURAL BRA

[75] Inventor: Theo Jose Cohen, Rio de Janeiro, Brazil

[73] Assignee: Cotrauma-Centro Ortopedico Traumatologico Ltda., Rio de Janeiro, Brazil

[21] Appl. No.: 555,599

[22] Filed: Nov. 9, 1995

[30] Foreign Application Priority Data

May 8, 1995 [BR] Brazil .............................. PI950 1947-2

[51] Int. Cl.$^6$ .................. A41C 3/02; A41C 3/12
[52] U.S. Cl. .................. 450/1; 450/17; 450/86; 2/44; 2/73; 602/19
[58] Field of Search .................. 2/44, 45, 92, 73, 2/109, 110, 268, 267, 105, 106, 113, 114, 115; 450/77, 79, 1, 80, 83, 86, 22, 23, 20, 21, 24, 155, 71, 17, 35; 602/19

[56] References Cited

U.S. PATENT DOCUMENTS

| | | | |
|---|---|---|---|
| 193,491 | 7/1877 | Du Laney | 450/83 |
| 657,133 | 9/1900 | Redick | 450/58 X |
| 664,214 | 12/1900 | Golden | 450/58 X |
| 811,167 | 1/1906 | Paddock | 2/92 |
| 1,494,119 | 5/1924 | Kops | 450/77 X |
| 2,054,330 | 9/1936 | Le May | 450/21 X |
| 2,477,792 | 8/1949 | Fratianni | 2/44 |
| 4,612,935 | 9/1986 | Greifer | 2/268 |
| 4,794,988 | 1/1989 | Reaver | 2/268 |
| 4,945,576 | 8/1990 | Melton | 2/268 |
| 5,098,331 | 3/1992 | Corrado | 450/58 |

*Primary Examiner*—Jeanette E. Chapman
*Attorney, Agent, or Firm*—Henderson Kill & Olick, P.C.

[57] ABSTRACT

A postural bra for supporting and protecting a woman's breasts, helps prevent and correct a tendency of hyperkyphosis of the backbone. The postural bra comprises a bra body (12), provided in its central front part with vertical shoulder lifters (14A, 14B) and of a posterior support (16). The bra body contains, in its lateral edges, identical straps (18A, 18B) which are connected at one of their edges, to upper parts of the vertical folds (20A, 20B) of the referred posterior support (16) and, in the other edges, to the lower parts of the horizontal folds (22A, 22B) of the referred posterior support (16), from which point adjusting straps (24A, 24B) are lengthened.

4 Claims, 4 Drawing Sheets

POSTURAL BRA

BACKGROUND OF THE INVENTION

The present invention refers to postural correction devices and more specifically to a postural bra for correcting and/or preventing hyperkyphosis, particularly women.

It is widely known in the medical field that at least one third of all women will suffer from osteoporosis beyond the age of menopause. The main osteoporosis symptom is a slow and progressive weakening of the bone structure. Usually after 35 years of age this condition occurs and is often completely unnoticed. As a consequence of this bone weakening, it is common for women beyond the age of menopause, to suffer a decrease in height, as well as to develop curvature of the spine which originates a gibbosity. This not only effects a person's appearance, but also causes pain, mainly in women who have led a sedentary life and have larger breasts. The initial problem basically concerns the posture. Afterwards, it affects the bones because of the flattening of the vertebrae, which, in this circumstance, turns to be irreversible. On the other hand, during the menopause period, many relevant changes in the woman's body may cause depression, which signals lack of interest to perform certain activities, leading to bad posture (hunchback), depression and pain.

From the above problems, we have learned that if it is possible to prevent this deformity, women will be able to walk more confidently, without shyness or discouragement, typical of people who walk leaning forward. This is caused by the aging process and affects a person's psychological condition.

It is therefore an object of the invention to provide a postural bra which promotes posture correction in a simple, efficient and comfortable way.

Another object of the invention is to provide a postural bra which lessens back muscle pain and irreversible wearing of the vertebrae.

SUMMARY OF THE INVENTION

These and other objects of the invention, which shall be apparent hereafter, are achieved by a postural bra which is made as a kind of vest involving the breast and shoulders and which is supported at the shoulders. The positioning of the postural bra has two different functions: to support and protect the user's breast and prevent and correct a possible tendency of hyperkyphosis of the backbone.

The postural bra is basically formed by the body of a bra provided, in its front part, with vertical strips which form bra cup separators, and by a posterior rigid support. The bra body includes, at its opposite lateral edges, identical straps which have ones of their ends connected, respectively, to the upper parts of two, extending vertically upward, arcuate portions of the posterior support, and have their other, opposite ends connected, respectively, to two, horizontally extending, opposite approximately thumb-shaped portions of the posterior support.

The body straps are associated each with an adjustable strap the end extension of which is provided with a VELCRO® fastener. The straps interconnect the body of the bra and the posterior support. The vertical strips, which form the bra cup separators, are provided with clasps, pressure buttons, and the like which insure a complete adaptation of the bra body to the breast portion of the body of the bra user. This insures proper and optimal positioning of the posterior support on the bra user's body.

BRIEF DESCRIPTION OF THE DRAWINGS

The invention will be better understood, by the Detailed Description of the Preferred Embodiment with reference to the drawings, of which.

DETAILED DESCRIPTION OF THE PREFERRED EMBODIMENT

Figure 1:
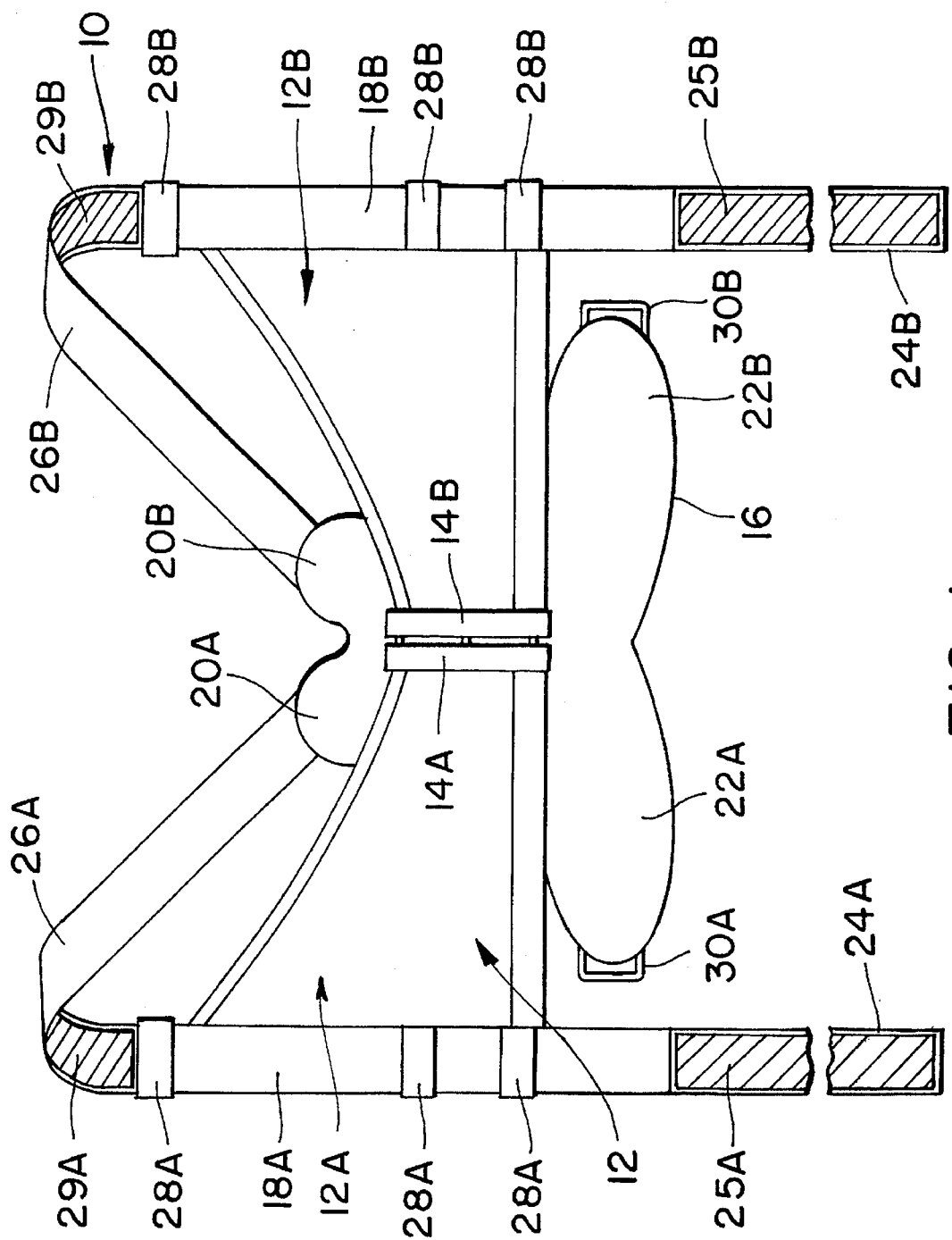
FIG. 1 represents a front perspective view of the postural bra.
Figure 2:
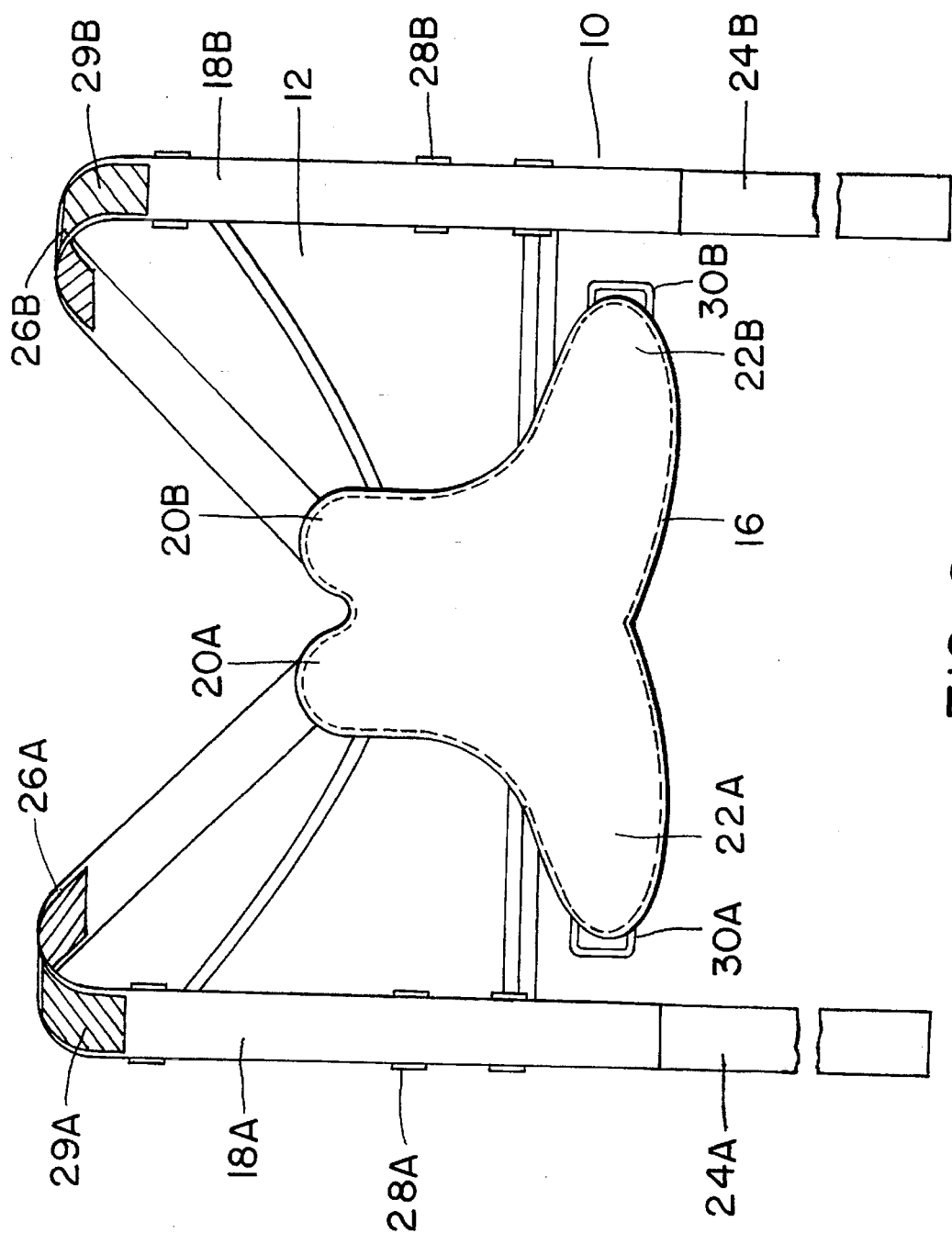
FIG. 2 represents a posterior perspective view of the postural bra.
Figure 3:
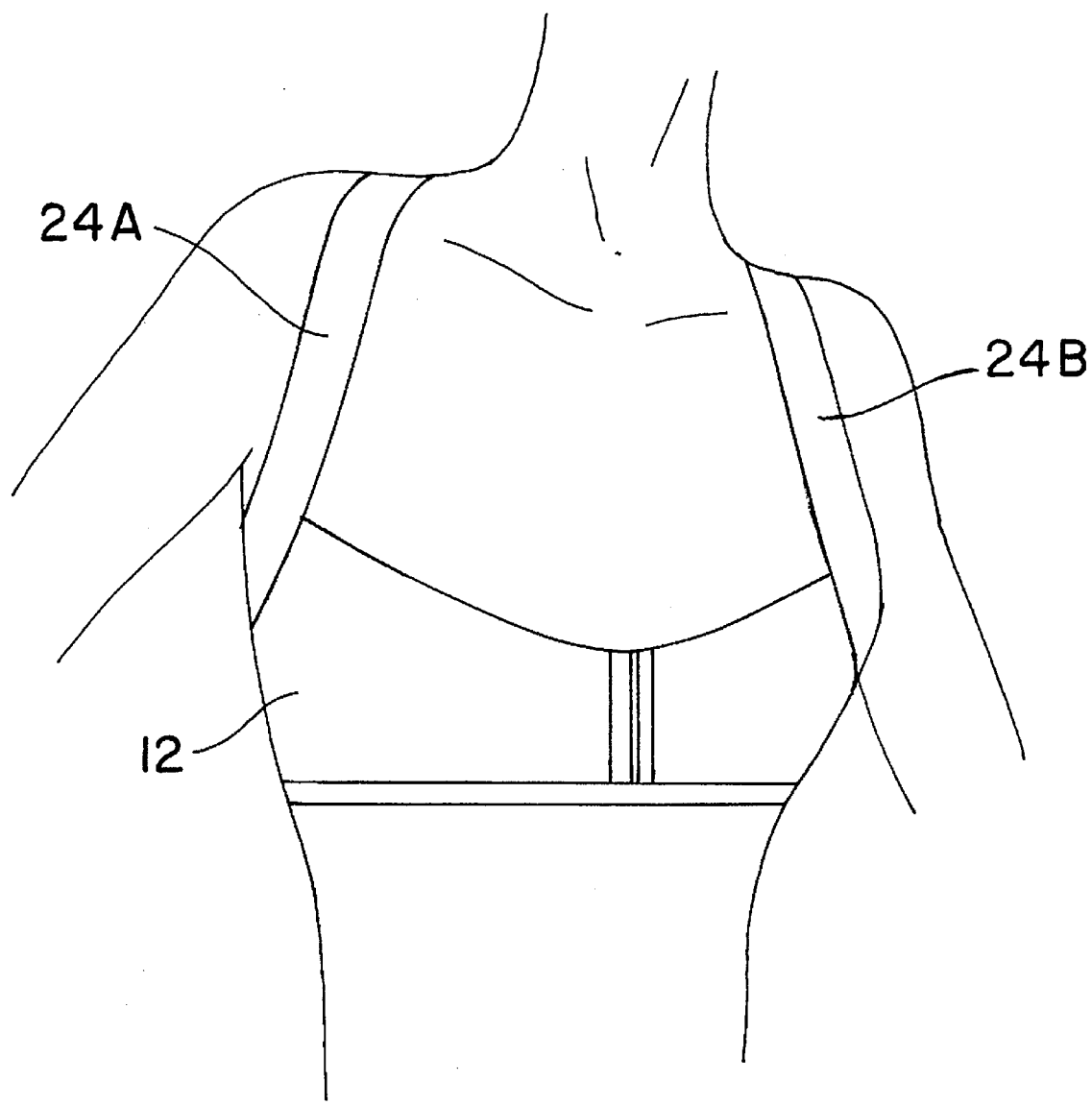
FIG. 3 represents a perspective view of the postural bra, applied to a woman's breasts in a front view, where the front buttoning is with clasps.
Figure 4:
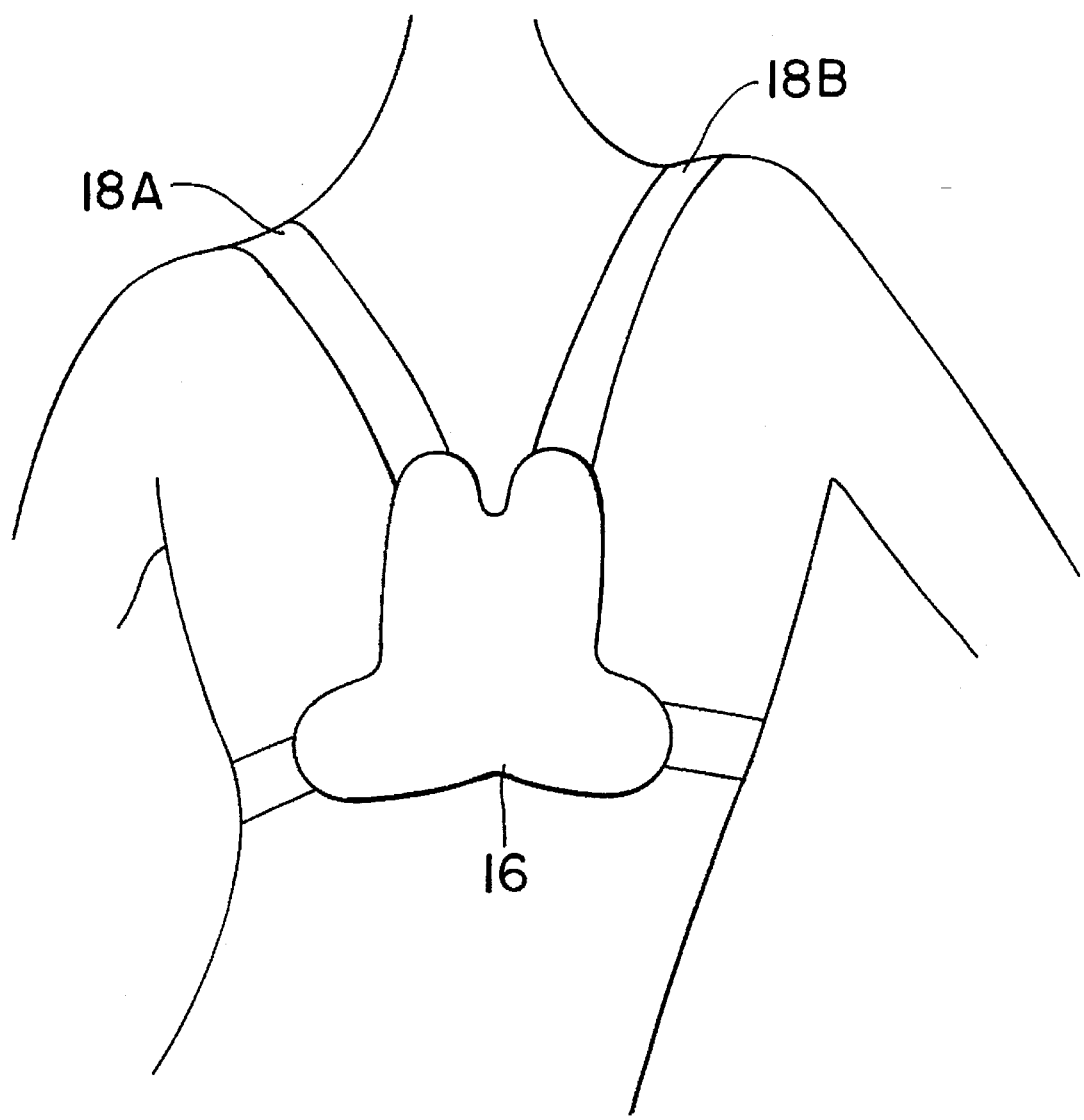
FIG. 4 represents a perspective view of the postural bra, applied to a woman's breasts seen from her back.

Referring now to the figures, wherein like numerical references identify correspondent parts, the postural bra is generally indicated by the numeral 10 and basically comprises a bra body 12 formed of two halves 12A and 12B which define breast cups and are provided at their adjacent lateral edges with strips 14A, 14B. The strips 14A and 14B are provided with appropriate means such as hooks, clasps, etc. for their adjustable attachment with each other to thereby insure adaptation of the bra body to the user's breast.

The bra body halves 12A and 12B have, at their remote lateral edges, identical straps 18A, 18B one ends of which are connected, respectively, to the upper parts of two, extending vertically upward arcuate portions 20A, 20B of a posterior rigid plastic support 16. The opposite other ends of the straps 18A, 18B are connected, respectively, to two, horizontally extending, lower, approximately thumb-shaped portions 22A, 22B of the posterior support 16.

The straps 18A, 18B are provided with adjusting straps portions 24A, 24B, respectively. The adjusting strap portions 24A, 24B have posterior extensions 25A, 25B provided with VELCRO® fasteners. The anterior portions of the straps 18A, 18B are provided with conventional strap adjusters 28A, 28B for adjusting the effective length of the straps 18A, 18B. The shoulder portions 26A, 26B of the straps 18A, 18B are provided with VELCRO® fasteners 29A, 29B, which cooperates with the fasteners of extentions 25A, 25B for securing the bra on the wearer.

The horizontally extending lower portions 22a, 22B of the posterior support 16 are provided at their free ends with metal guides 30A, 30B for the adjustable straps 24A, 24B when the adjusted straps are attached to the should straps 18A and 18B. The strap adjusters 28A, 28B, the VELCRO® fasteners 29A, 29B, and the guides 30A, 30B insure proper positioning of the postural bra on the user's body and a complete adaptation of the postural bra to the user's body.

While the adjustment of the bra upon putting it on should be clear from the foregoing description of its constructions, for completeness sake, the process of putting the bra on will now be described. Upon putting the bra on, the two vertical strips 14A and 14B are connected with each other, encompassing the breast. Thereafter, the bra wearer pulls down the straps 18A and 18B down, pulling back the shoulders. Thereafter, the adjusting strap portions 24A, 24B are passed through the ring-shaped guides 30A, 30B and then through respective strap adjusters 28A, 28B. Having adjusted the strap length, the adjusting strap portions 24A, 24B are attached to the shoulder portions 26A, 26B, with the VELCRO® fasteners provided at the extensions 25A, 25B engaging the VELCRO® fasteners 29A, 29B of the should portions 26A, 26B.

This arrangement causes the breasts to be firmly held up with support at the shoulders. It also results in more even weight distribution. On the other hand, the user keeps a permanent erected position, because the provision of the posterior elastic support 16 which makes direct contact with the user's back and its interconnection with the shoulder strap portions 26A, 26B forces a "natural straightening." This results in a permanent erect posture, avoiding curvature of the spine, which occurs simultaneously with an adequate support of the breast, preventing the tendency of hyperkyphosis of the backbone, as mentioned before.

It should be understood that the postural bra can be manufactured with any kind of material and for any size breasts and may also include specific details which cause it to be more appropriate to particular use conditions.

While the preferred embodiment of the invention has been depicted in detail, modifications and adaptations may be made thereto, without departure from the spirit and scope of the invention as delineated in the following claims:

What is claimed is:

1. A postural bra, comprising:

a bra body formed of two breast cups provided at adjacent lateral edges thereof with vertical strips adjustably connectable with each other;

a posterior support having two upwardly extending vertical portions and two horizontal portions provided at respective lower ends of the vertical portions; and two straps provided, respectively, at remote lateral portions of the cups and connected at one end portions thereof to upper portions of the vertical portions of the posterior support and adjustably connected to free ends of the horizontal portions of the posterior support, the two straps having respective adjusting end strap portions for adjusting the bra on a wearer's body, wherein the free ends of the horizontal portions of the posterior support are provided each with a guide for a respective strap to provide for attachment of the straps to the horizontal portions of the posterior support, and wherein the two straps have respective should portions provided with first fasteners, respectively, and the adjusting strap portions are provided, at free ends thereof with second fasteners cooperating with the first fasteners for adjustably securing the bra on the wearer's body after attachment of the two straps to the posterior support.

2. The postural bra of claim 1, wherein the first and second fasteners are formed as VELCRO® fasteners.

3. The postural bra of claim 1, wherein anterior portions of the two straps are provided, respectively, with strap adjuster means through which the adjusting strap portions are extendable for adjusting the bra.

4. The postural bra of claim 1, wherein the posterior support is formed of a semi-rigid plastic material.

* * * * *